(12) United States Patent
Knight

(10) Patent No.: US 9,545,633 B2
(45) Date of Patent: *Jan. 17, 2017

(54) HEAT TRANSFER BAFFLE SYSTEM AND USES THEREOF

(71) Applicant: ABEC, Inc., Bethlehem, PA (US)

(72) Inventor: Cameron Knight, Springfield, MO (US)

(73) Assignee: ABEC, Inc., Bethleham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/166,208

(22) Filed: Jan. 28, 2014

(65) Prior Publication Data

US 2014/0246182 A1 Sep. 4, 2014

Related U.S. Application Data

(63) Continuation of application No. 12/605,329, filed on Oct. 24, 2009, now Pat. No. 8,658,419.

(60) Provisional application No. 61/240,029, filed on Sep. 4, 2009.

(51) Int. Cl.
| | |
|---|---|
| *B01L 7/00* | (2006.01) |
| *C12M 1/00* | (2006.01) |
| *B01J 8/00* | (2006.01) |
| *B01J 8/20* | (2006.01) |
| *B01J 19/00* | (2006.01) |
| *B01J 19/18* | (2006.01) |
| *F28D 9/00* | (2006.01) |
| *F28F 9/02* | (2006.01) |
| *F28F 13/12* | (2006.01) |
| *F28F 9/22* | (2006.01) |
| *F28D 21/00* | (2006.01) |

(52) U.S. Cl.
CPC ........... *B01L 7/00* (2013.01); *B01J 8/008* (2013.01); *B01J 8/20* (2013.01); *B01J 19/006* (2013.01); *B01J 19/18* (2013.01); *F28D 9/0006* (2013.01); *F28D 9/0025* (2013.01); *F28F 9/0246* (2013.01); *F28F 9/22* (2013.01); *F28F 13/12* (2013.01); *B01J 2208/0084* (2013.01); *B01J 2208/00212* (2013.01); *B01J 2219/00085* (2013.01); *B01J 2219/00768* (2013.01); *B01L 2300/1805* (2013.01); *B01L 2300/1838* (2013.01); *F28D 2021/0022* (2013.01)

(58) Field of Classification Search
CPC .............. B01L 17/00; B01L 2300/1838; B01L 2300/1805; B01J 19/006; B01J 19/18; B01J 2208/00212; B01J 2208/0084; B01J 2219/00085; B01J 2219/00768; F28F 9/22; F28F 9/0246; F28F 13/12; F28D 2021/0022
See application file for complete search history.

(56) References Cited

U.S. PATENT DOCUMENTS

| 3,400,051 A | 9/1968 | Hofschneider |
| 4,670,397 A * | 6/1987 | Wegner et al. ............ 435/289.1 |
| 2004/0154331 A1 | 8/2004 | Horiuchi et al. |
| 2007/0096611 A1 | 5/2007 | Antonijevic et al. |

(Continued)

FOREIGN PATENT DOCUMENTS

EP 1172138 B1 7/2005

*Primary Examiner* — Michael Hobbs
(74) *Attorney, Agent, or Firm* — Patrick J Halloran

(57) ABSTRACT

This disclosure describes an improved heat transfer system for use in reaction vessels used in chemical and biological processes. In one embodiment, a heat transfer baffle comprising two sub-assemblies adjoined to one another is provided.

20 Claims, 9 Drawing Sheets

(56) References Cited

U.S. PATENT DOCUMENTS

2007/0169916 A1* 7/2007 Wand et al. .................. 165/70
2009/0145591 A1* 6/2009 Rericha et al. .............. 165/174
2010/0303682 A1 12/2010 Rizzi et al.
2012/0011867 A1* 1/2012 Koons et al. ................. 62/115

* cited by examiner

HEAT TRANSFER BAFFLE SYSTEM AND USES THEREOF

RELATED APPLICATIONS

This application is a continuation of U.S. Ser. No. 12/605,329 filed Oct. 24, 2009, now U.S. Pat. No. 8,658,419 B2, which claims priority to U.S. Ser. No. 61/240,029 filed Sep. 4, 2009, each of which are incorporated herein by reference in their entirety.

FIELD OF DISCLOSURE

In certain embodiments, the heat transfer baffle may be constructed by mechanically assembling its various parts. For instance, the heat transfer baffle may be assembled by joining two or more heat transfer sub-assemblies adjoined to one another in a "back-to-back" configuration and being in communication with flow distribution ("inlet") and collection ("outlet") headers as provided. The heat transfer sub-assemblies are typically fabricated from a first material (e.g., dimple-jacket material) adjoined (e.g., welded) to a second material (e.g., a support material). In certain embodiments, the materials are adjoined to form channels for the transport of heat transfer media (e.g., "distribution channels"). For instance, the gaps between the first and second materials may form distribution channels through which heat transfer media may circulate or flow. Two sub-assemblies are typically affixed to one another. When two sub-assemblies are adjoined to one another, two distribution channels (e.g., one within each sub-assembly) and one relief channel (e.g, between the sub-assemblies) are typically formed within a single heat transfer baffle. The sub-assemblies may be adjoined to one another by any suitable method (e.g., welding, adhesive). Where the material is a form of metal, welding may be particularly useful but other methods may also be useful. For instance, the sub-assemblies may be adjoined using a third material fashioned into a connecting piece or "closure bar". This material is typically in communication with each sub-assembly, thereby adjoining the sub-assemblies to one another. The width of this material typically determines the diameter of the relief channel, and accordingly may be adjusted as desired.

BACKGROUND INFORMATION

This disclosure relates to equipment having reaction vessels used to manufacture chemical and/or biological products such as biopharmaceuticals. For instance, fermentors commonly provide a reaction vessel for cultivation of microbial organisms or mammalian, insect, or plant cells to produce such products. It is important to control the temperature of the reaction to ensure optimal production of the product. For example, fermentations typically produce excess heat that must be dissipated or removed from the system to ensure proper reaction conditions. Those of skill in the art have suggested various systems for controlling the temperature within reaction vessels, as briefly reviewed below. However, there remains a need in the art for improved heat control systems that also incorporates the use of sanitary material surfaces, such as that provided herein.

Previously available systems are described in several U.S. and foreign patents. For instance, U.S. Pat. No. 2,973,944 (Etter, et al.) describes a system of "individual coil units" that each contain a group of tubes that serve as heat transfer elements in a reaction vessel. The units are indirectly affixed to the inner part of the vessel using bracing members located at the top, bottom, and/or throughout the length of each unit. The '944 patent points out that an advantage of such indirect attachment is that the expansion and contraction units during will not damage the reactor shell. The units described by the '944 patent are not internal, e.g., part of a baffle, but instead consist of multiple tubes fully exposed to the reaction vessel. Another tube-based system is described in U.S. Pat. No. 3,986,934 (Muller, H.) which provides a baffle including multiple tubes, the baffle being positioned substantially in the center of the reaction vessel. The fermentation media is circulated through the baffle such that is contacts the tubes containing the heat transfer media to optimize contact between the reaction components and the heat transfer media. And U.S. Pat. No. 4,670,397 (Wegner, et al.) discloses a system of tube baffles spaced approximately evenly around the fermentor circumference. The baffles that are positioned apart from the fermentor wall, thereby providing a space between the outer shell of the fermentor and the baffles.

U.S. Pat. No. 4,985,208 (Sugawara, et al.) illustrates a polymerization reaction apparatus including multiple heat transfer elements attached to the inner wall of the reaction vessel between agitating blades. Heat transfer medium may be circulated within an internal passage of the heat transfer elements. The internal passage may be formed in a "zigzag" pattern provided using alternately disposed reinforcing plates. Similarly, U.S. Pat. No. 4,460,278 (Tetsuyuki, et al.) discloses a cylindrical vessel with heat exchangers installed between agitating blades.

Commercially available systems currently offered by manufacturers (e.g., Tranter, Paul Mueller, Omega) include platecoils, spiral-wound pipe systems, and other vertical pipe loop systems. For instance, the Platecoil® system provides heat transfer elements constructed from two metal sheets that are resistance welded together to form passages through which heat transfer media is circulated. Platecoils are available in various forms and are suitable for insertion within a reaction vessel.

The currently available systems do not provide both sufficient structural integrity for use in high power-per-volume reactors and sanitary construction. The heat transfer systems described herein include a baffle described that solves these problems. As described below, the baffle typically has distribution channels through which heat transfer media is circulated and one or more relief channels through which heat transfer media is not circulated, which may also function as a vent for the distribution channels. This construction provides exceptional structural integrity. The baffle is also typically affixed to the reaction vessel such that substantially no seams appear between the baffle and the vessel, thereby providing a surface suitable to sanitization.

SUMMARY OF THE DISCLOSURE

Provided herein are heat transfer systems that efficiently transfer heat, withstand the hydraulic forces encountered within a reaction vessel, and may be simply and efficiently sanitized. The heat transfer baffle described herein may be incorporated into heat transfer systems to solve these problems. In certain embodiments, the baffle has at least one internal channel and at least two external channels. Typically, heat transfer media is circulated through the distribution channels but not the one or more relief channels, which may also function as a vent(s) for the distribution channels. The incorporation of distribution and relief channels into the baffle provides exceptional heat transfer capabilities and the structural integrity necessary to withstand the hydraulic forces encountered in a reaction vessel. Additionally, the baffle is typically affixed to the reaction vessel such that no seams appear between it and the vessel, thereby providing a surface suitable to sanitization.

DETAILED DESCRIPTION

Figure 1:
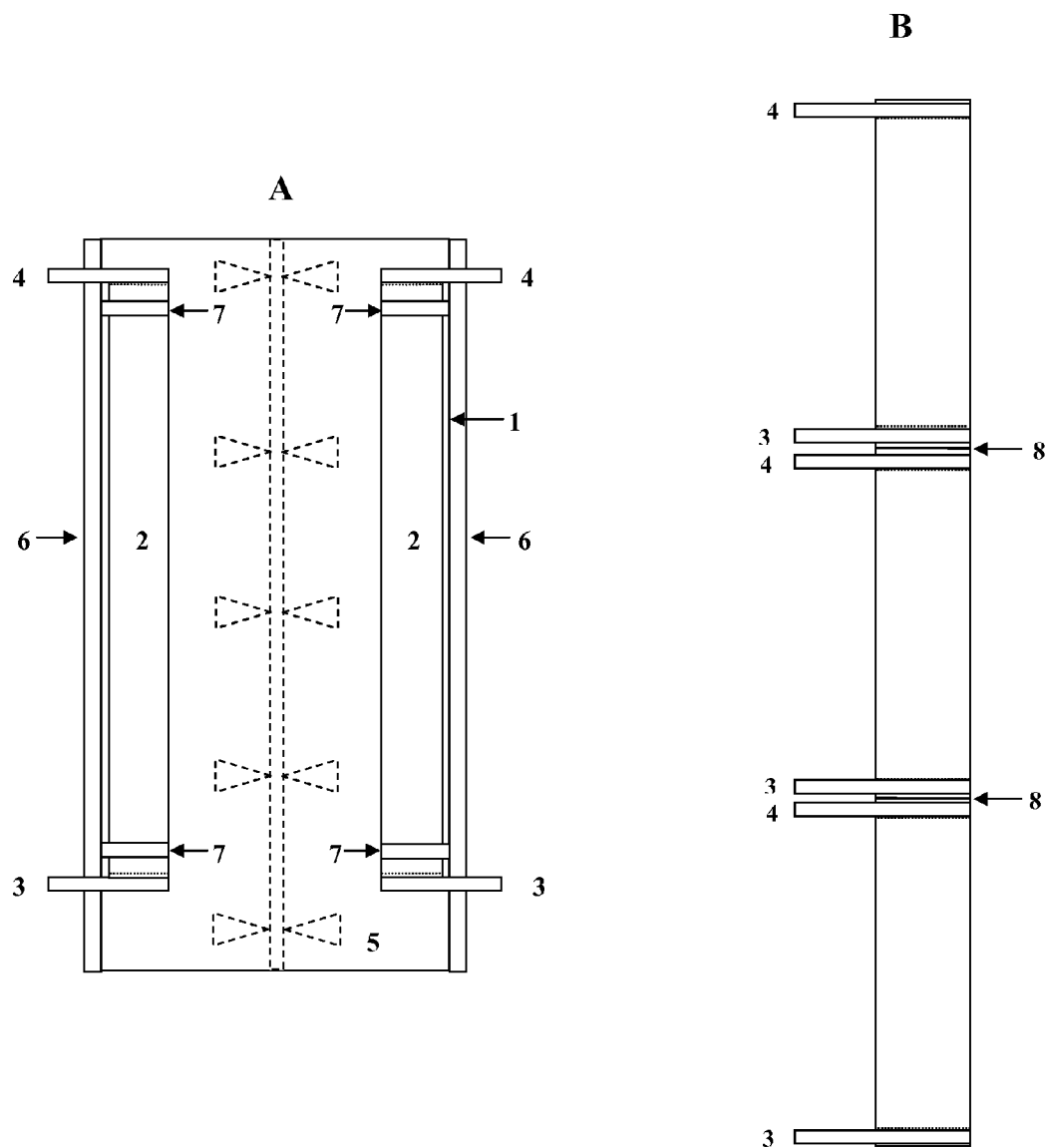
FIG. 1. A. Exemplary embodiment of the reaction vessel equipped with multiple heat transfer baffles as described herein. B. Exemplary multi-zone heat transfer baffle.
Figure 2:
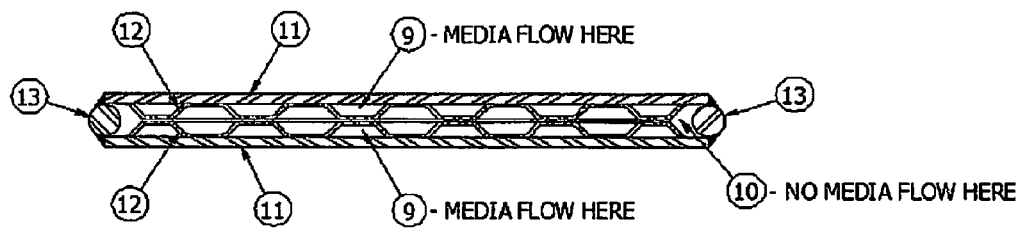
FIG. 2. Exemplary heat transfer baffle construction.

Described herein are heat transfers systems for use in a reaction vessel. Exemplary reaction vessels may take the form of a chamber, fermentor, bioreactor, or the like, and/or those typically used in chemical reactions, fermentation of microbial organisms, and/or the cultivation of cells (e.g., mammalian, insect or plant-based). A common problem associated with the use of such reaction vessels is temperature control. The reactions are many times extremely exothermic or endothermic, and extreme changes in temperature may affect chemical reactions, cell growth, and the like. The systems described herein provide a robust and novel solution to such problems, such that the temperature within a reaction vessel may be precisely controlled. The heat transfer systems described herein efficiently transfer heat, withstand the hydraulic forces encountered within a reaction vessel, and may be simply and efficiently sanitized.

The heat transfer systems described herein typically include at least one heat transfer baffle. In certain embodiments, the heat transfer baffle has one or more distribution channels and at least one relief channel. Depending upon the embodiment, the baffle may contain a single relief channel or multiple relief channels. To indicate this option, this description may refer to the relief channels as relief channel(s) which indicates "one or more relief channels". The distribution channels are typically found nearest the exterior of the baffle, and thereby closer to the reaction chamber than the relief channel(s), to provide sufficient heat transfer surface area to the reaction chamber interior. The relief channel(s) are typically found between the distribution channels but may also be alternatively or additionally between or external thereto. Heat transfer media is typically circulated through the distribution channels but not the relief channel(s). The relief channel(s) are typically directly or indirectly vented to the tank exterior through one or more relief holes (e.g., an orifice) to provide both a means of detecting failure (e.g., leakage) of an distribution channel and/or preventing the build-up of excess pressure. This ensures compliance with applicable codes for construction of pressure-containing equipment. This configuration provides a reinforced cross-section, thereby increasing the mechanical strength of the baffle. Venting of the relief channel to the exterior of the reaction chamber may be accomplished by placing one or more relief holes within such closure bars, for example. The use of such a baffle structure including the distribution and relief channels into the baffle provides exceptional heat transfer capabilities and the structural integrity necessary to withstand the hydraulic forces encountered in a reaction vessel (e.g., in an agitated reaction, high agitator power input per unit volume). The baffle may be formed of any suitable material as described herein and constructed using any available method. For instance, the baffle may be constructed by assembling various parts (see below) or using a molding or other technique (e.g., where a moldable material such as plastic is utilized). Described below is a method for assembling the baffle from its component parts but it should be understood that many other methods may be suitable. As such, it is to be understood that a heat transfer baffle having two or more distribution channels for circulation of heat transfer media and at least one relief channel is described herein. The baffle may be constructed, made or assembled by any suitable method, using any suitable material as described herein or as may otherwise be available to the skilled artisan. Similarly, the baffle may be incorporated into, attached or affixed to a reaction vessel by any suitable method provided that method provides a substantially seamless attachment point (e.g., a seamless joint or boundary between materials) to provide a surface that may be simply and efficiently sanitized. A "substantially seamless attachment point", "seamless joint", or "crevice-free joint" typically indicates that the boundary between the baffle and the reaction vessel is substantially undetectable by either visual and/or other means (e.g., microscopy). It may also indicate that the boundary does not retain any residue from prior reactions following a standard cleaning procedure typically used by the skilled artisan to "sanitize" such equipment. The system is therefore suitable for sanitization using industry-accepted "clean-in-place" and "sterilize-in-place" systems using any suitable cleaning agent including but not limited to detergents, brushes, and/or steam. Such a boundary affords itself to simple and efficient sanitization, as defined below.

A surface may be considered sanitized if it is considered "clean" by one of skill in the art. A surface may be considered sanitized if it is "sanitary" as defined by the American Society of Mechanical Engineers (ASME) with respect to bioprocessing equipment, such as "pertaining to equipment and piping systems that by design, materials of construction, and operation provide for the maintenance of cleanliness so that the products produced by these systems will not adversely affect human or animal health." A surface may also be considered sanitized when it is free from microorganisms including but not limited to living or non-living bacteria and/or viruses, and/or is aseptic as is commonly understood in the art. For chemical reactions, a sanitized surface is one that is substantially free of any detectable chemical residue on the surface that may be inadvertently incorporated into or otherwise adversely affect production of the reaction product, the recovery thereof from the vessel, or its use following recovery, for example. It would be understood by those of skill in the art that contamination of a product to be administered to a human or animal with an organism or compound not intended to be included in that product could "adversely affect" the health of that human or animal. Surfaces containing such contaminants are therefore not considered "sanitized" for the purposes of this disclosure.

The distribution channels are typically formed by adjoining at least two materials to one another such that one or more channels are formed between those materials. It through these channels that heat transfer media is circulated. The channels may be of any form as long as sufficient heat transfer surface area is provided thereby. For instance, the channels may be straight, serpentine, "zig-zag", etc. A channel may also be regular or irregular, as may be found in a dimple jacket material. The distribution channels may also be formed from a single material (e.g., plastic) as described herein. Other embodiments of the distribution channels as would be known to one of skill in the art are contemplated herein.

In certain embodiments, the heat transfer baffle may be constructed by mechanically assembling its various parts. For instance, the heat transfer baffle may be assembled by joining two or more heat transfer sub-assemblies adjoined to one another in a "back-to-back" configuration and being in communication with flow distribution ("inlet") and collection ("outlet") headers as provided. The heat transfer sub-assemblies are typically fabricated from a first material (e.g., dimple jacket material) adjoined (e.g., welded) to a second material (e.g., a support material). In certain embodiments, the materials are adjoined to form channels for the transport of heat transfer media (e.g., "distribution channels"). For instance, the gaps between the first and second materials may form distribution channels through which heat transfer media may circulate or flow. Two sub-assemblies are typically affixed to one another. When two sub-assemblies are adjoined to one another, two distribution channels (e.g., one within each sub-assembly) and one relief channel (e.g, between the sub-assemblies) are typically formed within a single heat transfer baffle. The sub-assemblies may be adjoined to one another by any suitable method (e.g., welding, adhesive). Where the material is a form of metal, welding may be particularly useful but other methods may also be useful. For instance, the sub-assemblies may be adjoined using a third material fashioned into a connecting piece or "closure bar". This material is typically in communication with each sub-assembly, thereby adjoining the sub-assemblies to one another. The length of this material typically determines the diameter of the relief channel, and accordingly may be adjusted as desired.

The heat transfer baffle may also comprise a first material joined to a second material such that one or more distribution channels are formed, which may be affixed to another material using a closure bar or the like. As such, the heat transfer baffle would have the distribution channel(s) on one side of the baffle, and the relief channel on the other side. The baffle could also be constructed with relief channels exterior to one or both distribution channels. As such, the baffle could be designed to contain, for instance, one, two, three or more relief channels that may be between, near or surrounding the distribution channels. This heat transfer baffle may then be attached to the reaction vessel as described herein (e.g., using attachment arms). Certain of these embodiments may be useful where, for instance, more or less heat transfer surface area is required.

The heat transfer baffle is typically attached to the reaction vessel, preferably to the interior wall thereof. As described above, any method of attachment may be used that provides a substantially seamless attachment point (e.g., a seamless joint or boundary between materials). The baffle may be attached directly to the reaction vessel, indirectly using another piece of material, or both directly and indirectly. The baffle may be positioned completely or partially against the interior wall of the vessel, or the baffle per se may not actually contact the interior wall of the vessel. For instance, attachment may be accomplished partially or completely indirectly using a fourth material (e.g., via one or more "attachment arms"). As described above, one advantage of the systems described herein is that the system may be efficiently sanitized. Attachment bars or the like may be particularly useful for this purpose. For instance, the attachment bars may be adjoined to the sub-assemblies by any suitable method and then adjoined to the reaction vessel surface using the same or other suitable method. Alternatively, the attachment arms may be adjoined to the reaction vessel surface and then attached to the sub-assemblies. The baffle may also be attached to the reaction vessel by, for example, welding the baffle directly to the reaction vessel. A combination of indirect attachment using, for example, attachment arms, and direct attachment (e.g., by welding the baffle directly to the reaction vessel) may also be utilized. Welding is a particularly useful method of attachment as the attachment bar material provides sufficient material for the deposition of a strong, ground and/or polished weld bead at the joint. The exterior of the completed assembly is typically mechanically polished and/or electro-polished as appropriate to produce a sanitary surface. In certain embodiments, such as when dimple jacket material is used within the subassemblies, the back-to-back orientation positions the usually difficult-to-clean dimple jacket materials on the interior of the sub-assembly and the support material, which is typically smooth and polished, on the exterior of the sub-assembly. In such an embodiment, the spaces between the dimple jacket material and a support material form the distribution channels, and the space between the juxtaposed dimple jacket material forms the relief channel. Such a configuration provides a heat transfer system with a sanitary structure that provides the desired heat transfer capabilities while also fulfilling the need for a structurally robust mechanical component (e.g., anti-swirl baffle) within a reaction vessel (e.g., during an agitated process).

Figure 4:
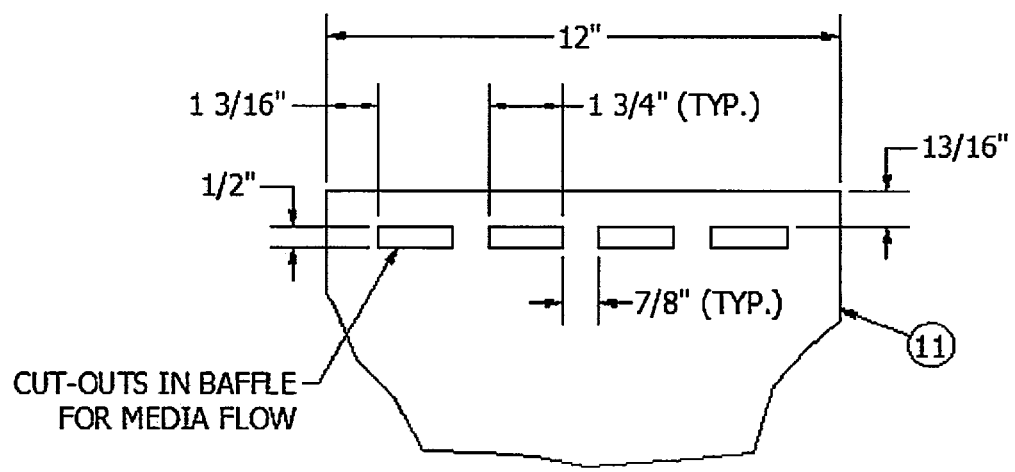
FIG. 4. Exemplary heat transfer media inlet/outlet cut-outs.
Figure 5:
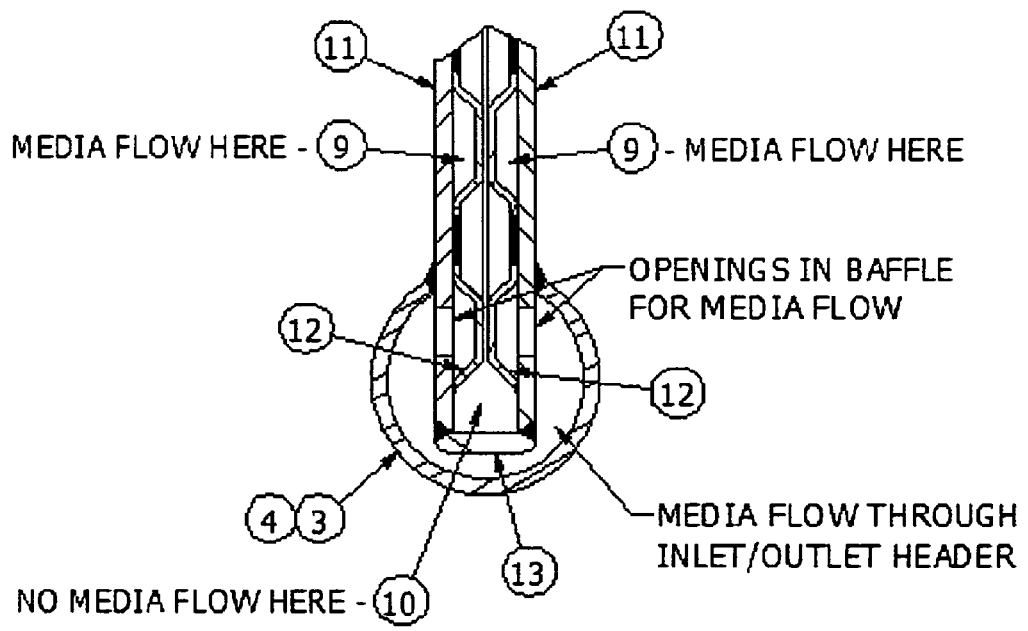
FIG. 5. Exemplary header construction.
Figure 6:
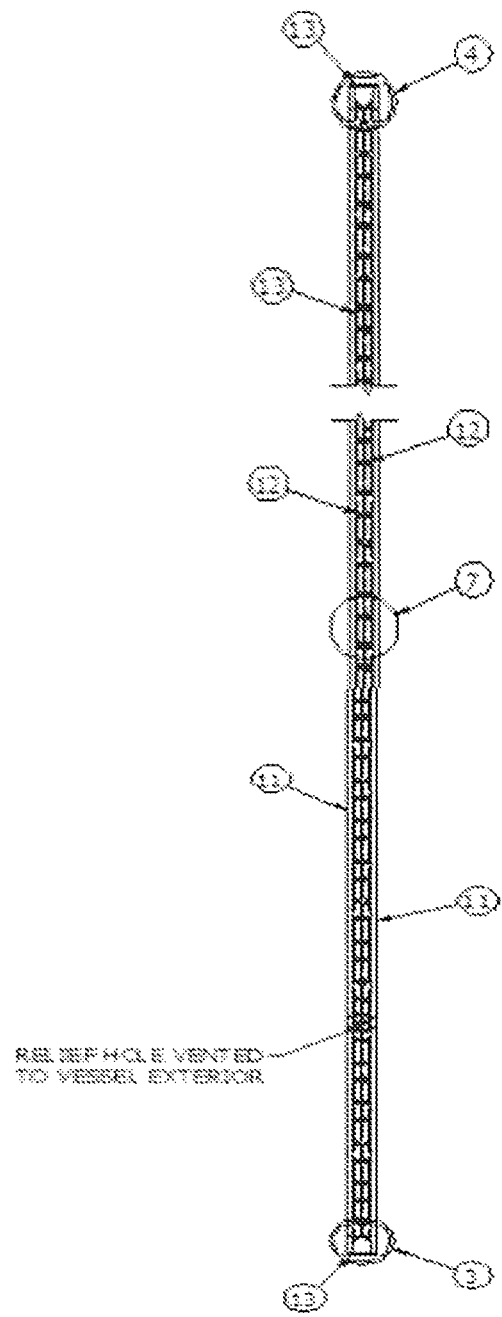
FIG. 6. Side-view of exemplary heat transfer baffle.
Figure 7:
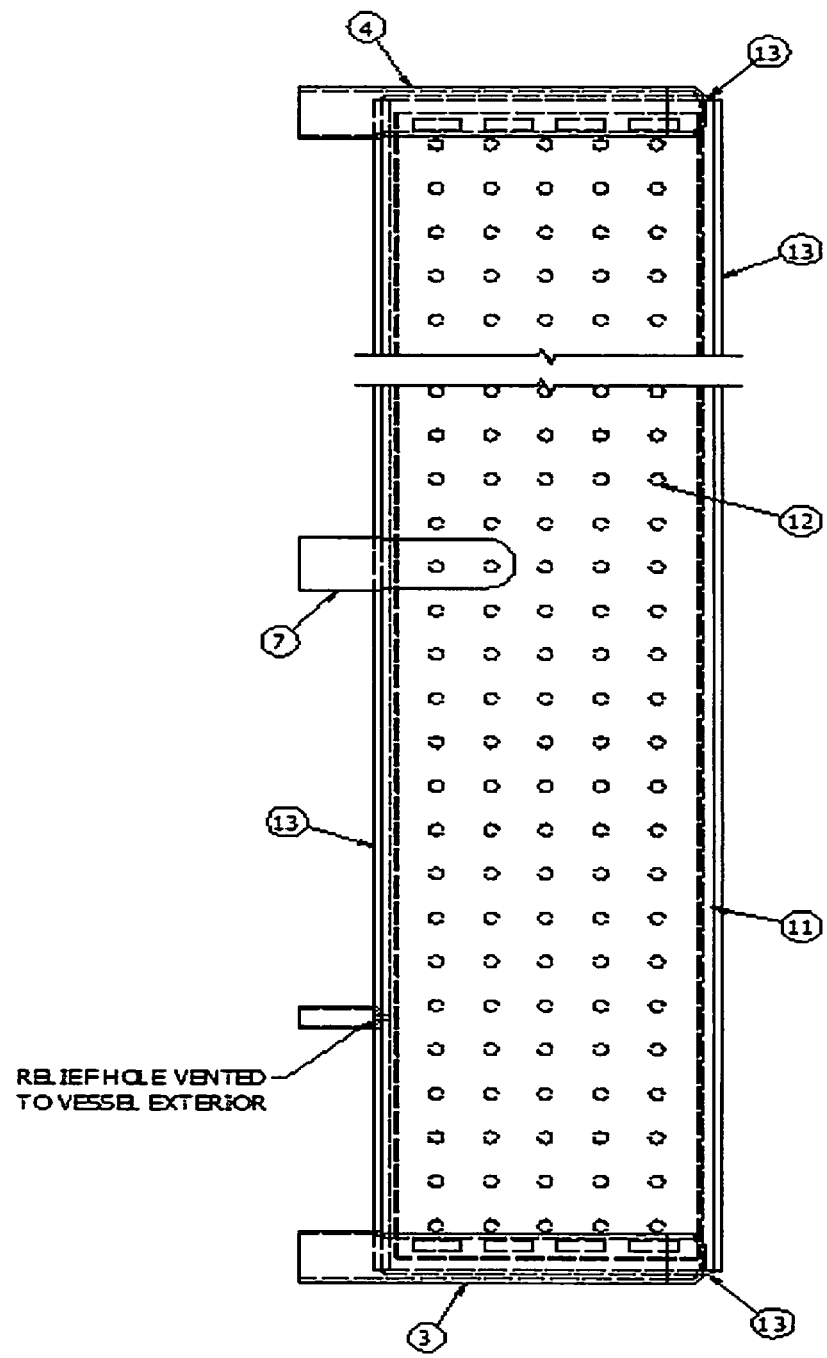
FIG. 7. Front-view of exemplary heat transfer baffle.

The heat transfer system also typically includes an inlet and outlet header used to transfer heat transfer media into and out of the baffle. The inlet header is typically in communication with an inlet pipe through which heat transfer media flows into the distribution channels of the baffle and the outlet header is typically in communication with an outlet pipe through which heat transfer media flows out of the distribution channels of the baffle. The relief channel(s) of the baffle are typically not in communication with either the inlet or outlet headers. The inlet and outlet headers distribute and collect heat transfer media flow to and from, respectively, the heat transfer sub-assemblies, provide uniform distribution of the heat transfer media across the entire width of the panel, and minimize flow short-circuits, thereby maximizing the effectiveness of the panel surface. In the event of a leak in the distribution channel, heat transfer media will be typically removed from the system through one or more relief holes which connect the relief channel(s) with the tank exterior. In the event of a leak in a distribution channel, the relief channel(s) provide a reservoir for the contents of the distribution channel to move, and an exit route from the reaction vessel or those contents (e.g., via the relief hole to the tank exterior). The inlet and outlet headers may be fabricated from any suitable material (e.g., pipe) in a tubular or other appropriate shape, terminating such that the header may be joined to the heat transfer media supply and discharge piping of the system. The inlet header is typically positioned on the baffle below the outlet header within the reaction vessel, but the inlet header may also be positioned on the baffle above the outlet header if desired. Accordingly, where the inlet header is positioned below the outlet header, the heat transfer fluid moves from the lower part to the upper part (e.g., bottom-to-top) of the baffle. Where the inlet header is positioned above the outlet header, the heat transfer medium moves from the upper part to the lower part (e.g., top-to-bottom) of the baffle. The inlet and outlet headers typically require one or more slots in the baffle material at the junction between the header and the exterior chambers of the baffle (e.g., FIG. 4). These slots are positioned such that flow into and out of the baffle is regulated but not adversely affected thereby (e.g., flow to and from the baffle is not restricted). The headers may come into contact with the baffle through the reactor vessel wall (e.g, from the side) or from within the reactor vessel, for example. Other suitable arrangements for moving heat transfer media into and out of the baffles may also be suitable, as would be understood by the skilled artisan.

Figure 3:
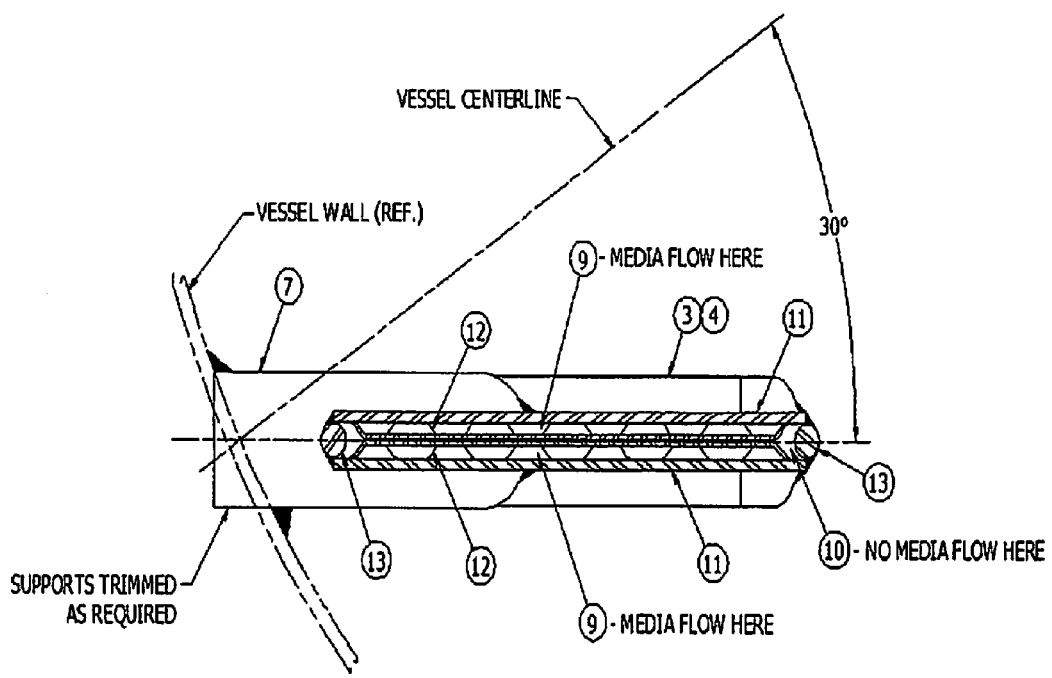
FIG. 3. Exemplary heat transfer baffle construction.

The reaction vessel may take any suitable form or shape, but is typically a vertical cylinder (e.g., it may also be horizontal). The baffles may protrude at regular or irregular intervals from the inner wall of the reaction vessel. The baffles may also be installed at any suitable angle relative to the inner wall of the reaction vessel (e.g., 60° relative to the interior wall, 30° relative to the radius, FIG. 3). A suitable angle may be an angle that would be understood by the skilled artisan to be appropriate in order to or sufficient to attenuate the forces (e.g., hydraulic forces) encountered by the baffles resulting from motion (e.g., rotational and/or swirl motion) of the vessel contents resulting from the agitation (e.g., mechanical or otherwise) thereof. A suitable angle is one that would prevent damage to the baffles from the forces resulting from such motion. Suitable angles include, for example, 5°, 10°, 15°, 20°, 25°, 30°, 35°, 40°, 45°, 50°, 55°, 60°, 65°, 70°, 75°, 80°, 85°, or 90° relative to either the interior wall of the vessel or the radius of the vessel. Where the reaction vessel contains a mechanism (e.g., mechanical or other mechanism) for agitating or mixing a reaction, such as a set of rotating blades or the like (e.g., an axial flow or radial flow impeller), the baffles are affixed to or protrude from the inner wall such that the mechanism and the baffles are not in contact with one another. For instance, where a device or devices for mixing the reaction components is located at the bottom center of the vessel, the baffles may be installed above the highest point of said means. Where multiple mechanical mechanisms are utilized, the baffles are typically configured to avoid those mechanisms. For instance, where the mechanism includes one or more sets of rotating blades, the baffle(s) may be positioned above, below, between or alongside the blades. The baffle design will ensure adequate clearance from the mechanical mechanisms.

The amount of heat transfer surface, and therefore the number and size of heat transfer baffles, required will vary depending on the type of reaction or reaction vessel. The amount required may be calculated by the skilled artisan using the available methods. As mentioned above, in an agitated reaction, the dimensions of the baffle may be determined at least in part by the type of mechanism being used for agitation. In other situations, the dimensions of the baffle may be determined by the size of the reaction vessel. For instance, in a cylindrical reaction vessel, the depth of the baffle, that is that portion of the baffle extending from the reaction vessel wall toward the interior of the vessel may be estimated to comprise roughly $\frac{1}{6}$ to $\frac{1}{12}$ (e.g., $\frac{1}{8}$, $\frac{1}{10}$) the diameter of the reaction chamber. However, it is to be understood that other arrangements may also be suitable.

Suitable heat transfer media include and are not limited to fluids and gases. Suitable fluids and gases include and are not limited to steam (top to bottom), hot and cold water, glycol, heat transfer oils, refrigerants, or other pumpable fluid having a desired operational temperature range. It is also possible to use multiple types of heat transfer media such that, for instance, one type of media is directed to one area of the reaction vessel and another type of media is directed to a different area of the reaction vessel (e.g., as in the zonal system described above). Mixtures of heat transfer media (e.g., 30% glycol) may also be desirable.

"Fixably attached", "affixed", or "adjoined" means that at least two materials are bonded to one another in a substantially permanent manner. The various parts described herein may be bonded to one another using, for example, welding, using an adhesive, or another similar process. The parts must remain attached to one another during use, meaning that the points of attachment (e.g., boundaries, joints) between the parts must be able to withstand the hydraulic forces encountered within the reaction vessel due to the motion of the reactor contents in response to the action of the agitator mechanism in addition to the pressures created from the heat transfer media flow.

The materials used to produce the equipment described herein may be of the same or different composition. The systems described herein are typically but not necessarily constructed from a corrosion-resistant alloy (e.g., metal). For instance, suitable materials may include, without limitation, dimple jacket material and/or sheet/plate stock. Suitable materials include, for example, carbon steel, stainless steel (e.g., 304, 304L, 316, 316L, 317, 317L, AL6XN), aluminum, Inconel® (e.g., Inconel 625, Chronin 625, Altemp 625, Haynes 625, Nickelvac 625 and Nicrofer 6020), Incoloy®, Hastelloy (e.g., A, B, B2, B3, B142T, Hybrid-BC1, C, C4, C22, C22HS, C2000, C263, C276, D, G, G2, G3, G30, G50, H9M, N, R235, S, W, X), and Monel®, titanium, Carpenter 20®, among others. It is understood, however, that other materials besides or in addition to a corrosion-resistant alloy such as, but without limitation, plastic, rubber, and mixtures of such materials may also be suitable. A "mixture" of materials may refer to either an actual mixture per se to form a combined material or the use of various materials within the system (e.g., an alloy reactor shell and rubber baffle components). Regarding the channeled material referred to above, any of the suitable materials described above may be prepared such that channels are formed through which heat transfer media may be distributed.

As mentioned above, one particularly suitable material that may be used in the baffle is dimple jacket material. Dimple jackets are typically installed around reaction vessels such as fermentation tanks and may be used as part of a heat transfer system. Dimple jacket material may be used in the devices described herein in the typical fashion, e.g., wrapped around the reaction vessel. In certain embodiments described herein, dimple jacket material may be also or alternatively used within the baffle structure. Dimple jacket materials are commercially available, and any of such materials may be suitable for use as disclosed here. Typically, dimple jacket materials have a substantially uniform pattern of dimples (e.g., depressions, indentations) pressed or formed into a parent material (e.g., a sheet of metal). Dimple jacket materials may be made mechanically ("mechanical dimple jacket") or by inflation (e.g., inflated resistance spot welding (RSW)), for example. To prepare a mechanical dimple material, a sheet of metal having a substantially uniform array of dimples pressed into, where each dimple typically contains a center hole, is welded to the parent metal through the center hole. An inflated RSW dimple material is typically made by resistance spot welding an array of spots on a thin sheet of metal to a more substantial (e.g., thicker) base material (e.g., metal). The edges of the combined material are sealed by welding and the interior is inflated under high pressure until the thin material forms a pattern of dimples. Mechanical dimple materials, when used as jackets, typically have high pressure ratings and low to moderate pressure drop, while RSW dimple jackets typically exhibit moderate pressure ratings and a high to moderate pressure drop. Other suitable dimple materials are available to those of skill in the art and would be suitable for use as described herein.

The reaction vessel may take the form of a reaction chamber, fermentor, bioreactor, or the like. The vessel is suitable for chemical reactions, fermentation of microbial organisms, cultivation of cells (e.g., mammalian, insect or plant-based), or other uses. The reaction vessel and associated heat transfer system may therefore be used in a method for controlling the temperature of a chemical, pharmaceutical or biological process in a vessel comprising an internal reaction chamber comprising at least one of the heat transfer assembly described herein. The process includes distributing a heat transfer medium through the heat transfer distribution channel of the at least one heat transfer assembly such that heat resulting from or required by the process is transferred from or to the reaction vessel by the heat transfer medium, thereby removing or adding heat from or to the reaction vessel. Other suitable applications of the systems described herein would be known to one of skill in the art.

Methods for controlling the temperature of a process in a reaction vessel by circulating heat transfer medium through the distribution channel of the at least one heat transfer baffle described herein are also provided. The methods may be used in, for example, a chemical process, a pharmaceutical process, a biological process, or other process. Biological processes may be, for example, a microbiological culture, mammalian cell culture, plant cell culture, or the like. The method may also be used in at least one step in the production of a vaccine. The method is typically be carried out by pumping a heat transfer fluid into the heat transfer baffle through, for example, the inlet header which is in communication with a source or reservoir of heat transfer fluid. The temperature of the heat transfer fluid is typically higher or lower than the temperature of the contents of vessel, depending on whether the temperature of the contents of the vessel are to be increased or decreased, respectively. The temperature of the heat transfer fluid may be adjusted as necessary in order to achieve the desired temperature of the vessel contents. The fluid is typically circulated through the heat transfer baffle and exits through, for example, the outlet header for further processing (e.g., heating or cooling) and/or re-circulation through the baffle. The temperature of the vessel contents is thereby altered to or maintained as desired by the user. Other suitable methods for using the systems described herein would be known to one of skill in the art.

An exemplary embodiment of the heat transfer system is shown in FIG. 1A. As shown therein, heat transfer baffle 2 is affixed to the interior 1 of reaction vessel 6 using attachment arms 7 (which may or may not extend to the entire width of the baffle). In the particular embodiment shown in FIG. 1A, the baffle is indirectly attached to the reaction vessel and does not directly contact the vessel. The baffle is typically in communication with inlet header 3 through which heat transfer fluid enters the baffle and an outlet header 4 through which heat transfer medium exits the baffle. In this embodiment, the baffles are attached to the reaction vessel above, below, or alongside a mechanism for mixing (5) the vessel contents. The mechanism for mixing the reaction components may be, e.g., an impeller system that may extend any length along the vessel as indicated by the dashed lines. Suitable impellar systems include but are not limited to, e.g., any manner and/or single and/or multiple and/or combination of axial flow and radial flow open impellers. The baffles are typically adjoined to the interior of the reaction vessel shell through attachment arms 7 by a welding or other process that results in a substantially seamless joint between the baffle and the reaction vessel. Thus, as typically constructed, the reaction vessel shell and the baffle may appear to form a single unit. This provides significant advantages in that the heat transfer system may be efficiently cleaned and/or sanitized, preferably leaving no residue at the joint.

The baffles may also be constructed such that heat transfer media is circulated within one or more compartments or zones of the baffle and therefore the reaction vessel. For instance, as shown in FIG. 1B, the baffles may be separated from one another by partition 8 to form independent intrabaffle compartments such that heat transfer media may be circulated through each compartment. The heat transfer media may be circulated through each compartment either in series or independently from any other compartment. Independent circulation typically requires each compartment or zone to comprise an inlet and outlet header attached for each compartment. The inlet and outlet headers may be in communication with one another or independent from one another. A valve or other mechanism for selecting particular baffles and/or inlet and/or outlet headers may also be provided. In this manner, heat transfer media may be circulated within particular areas (e.g., substantially the top, bottom, or middle) of the reaction vessel. This is useful where, for instance, the volume of the reaction is increased or decreased over time, such that more of less heat transfer surface area is required. The baffle may also be installed horizontally with respect to the reaction chamber, meaning that instead of running the top and bottom length of the chamber, the baffle would run across the chamber from side-to-side. Other suitable baffle orientations are contemplated herein as would be understood by one of skill in the art.

FIGS. 2, 3, and 5-7 illustrate exemplary baffles or portions thereof. As discussed above, the baffle is typically joined to inlet header 3 and outlet header 4. These headers are adjoined to the baffle such that the heat transfer media circulates through distribution channels 9. Relief channel(s) 10 are typically vented to the exterior of the vessel using, for instance, a relief hole (which may be found within a closure bar, for example). The inlet and outlet headers are not in communication with relief channel(s) 10, through which heat transfer media does not typically circulate due to design requirements regarding pressure containing equipment. Thus, the distribution and relief channels do not communicate, unless a leak forms within a distribution channel such that heat transfer medium or other material moves into the relief channel(s) and is vented from the baffle and reaction vessel. Distribution channels 9 are typically formed between the support material 11 and dimple jacket material 12 of each sub-assembly. Relief channel(s) 10 are typically formed by adjoining two sub-assemblies, each comprising support material 11 fixably attached to dimple jacket material 12 to one another. In such embodiments, the dimple jacket material and support material of each sub-assembly are typically adjoined to one another by welding or other process resulting in the materials being fixably attached to one another. The sub-assemblies are typically adjoined to one another using closure bars 13. The closure bar is typically adjoined to the support material by a welding or other process that results in a substantially seamless joint. The width of the closure bar may be adjusted to set the width of the relief channel as desired (e.g., setting the juxtaposed dimple jacket material closer together or further apart). One or more relief holes may be made within the closure bars such that relief channel(s) may communicate with the reaction vessel exterior. The baffle assembly is typically fixably attached to the vessel through attachment arm or arms 7 by a welding or other process that results in a substantially seamless joint. As described above, use of the attachment arms advantageously provides for efficient cleaning and/or sanitization of the baffles in that very little to no residue remains at the joint between the interior surface of the reaction vessel and the baffle following the attachment process (e.g., welding).

A better understanding of the present invention and of its many advantages will be had from the following examples, given by way of illustration.

EXAMPLES

Example 1

Baffle Construction

Construction of a heat transfer baffle as described herein was accomplished using essentially the steps described below:
1. The baffle material was cut to size. Heat transfer media inlet/outlet slots were cut in both ends of baffle material.
2. The baffle material was affixed into adequate jigs and fixtures to protect the baffle material from warping from heat build-up during the welding process. Warping can cause the baffle material to lose its desired shape.
3. Dimples were punched into the heat transfer material to create attachment points to weld heat transfer material onto baffle material. Punching the dimples in the heat transfer material creates an open 'pillow' section between the dimple spots. The creation of this 'pillow' section allows heat transfer media to flow properly throughout the heat transfer surface. The heat transfer material was cut to size and the edges crimped to allow the perimeter of the dimpled heat transfer surface to be welded to the baffle material.
4. The dimpled heat transfer material was welded onto baffle material. The welding sequence of the dimples and the perimeter edges was properly spaced in order to decrease the amount of heat build-up in the two materials being welded. Too much heat in any area at one time can cause the materials to warp, causing the baffle to lose its desired shape.

Note: In order to create one sanitary heat transfer baffle assembly, it is typically necessary to fabricate two sub-assemblies of baffle/heat transfer material as described in steps #1 through #4 above.

5. The baffle closure bars were cut to length.
6. Two baffle/heat transfer sub-assemblies were positioned with their heat transfer surfaces facing each other. The baffle material was aligned such that the surfaces were parallel with each other and the edges aligned.
7. The baffle closure bars were used to create the adequate spacing between the baffle/heat transfer sub-assemblies (e.g., thereby providing the relief channel(s)), and the weld closure bars were tacked in place. Final spacing, position and "squareness" of the baffle assembly was checked before final welding.
8. The baffle assembly was affixed into adequate jigs and fixtures to protect baffle assembly from warping from heat build-up during the welding process. Warping can cause the baffle assembly to lose its desired shape.
9. The baffle closure bars were then welded into position. The welding sequence of the baffle closure bars was spaced in order to decrease the amount of heat build-up in the materials being welded. Too much heat in any area at one time can cause the materials to warp, causing the baffle assembly to lose its desired shape.
10. The inlet/outlet header pipes were cut to length and header pipes notched along the middle of one side to accept baffle assembly.
11. The inlet/outlet header caps were notched along the middle to accept baffle assembly.
12. The baffle supports were cut to length and notches cut along the middle of one end to accept baffle assembly.
13. The inlet/outlet header pipes were welded into place.
14. The inlet/outlet header caps were welded into place.
15. The baffle supports were welded into place.
16. All welds were ground smooth and flush ensuring that no crevices are allowed. All surfaces are to be smooth with no crevices in order to achieve a sanitary finish.
17. The baffle assembly exterior surfaces are to be completely electro-polished if a smoother surface finish is required.

Example 2

Heat Transfer Testing

The heat transfer system was constructed essentially as described in Example 1 and tested using the following parameters:
1. Six (6) heat transfer baffles were installed in a vertical cylindrical vessel in the manner illustrated in FIG. 1A.
   i. Each baffle was 12" (305 mm) wide×168" (4,267 mm) long.
   ii. Baffles were installed at an angle of 30° relative to the vessel radius.
   iii. Baffles were oriented into the flow exiting the agitator impellers.
   iv. The vessel was 72" (1,829 mm) diameter×195" (4,953 mm) with ASME dished heads.
      1. Vessel total volume: 14,000 liters
      2. Vessel working volume: 10,000 liters
2. The vessel was equipped with a 100 hp (75 kW) agitator
   i. Agitator maximum speed: 159 rpm (2.65 s$^{-1}$)
   ii. Impeller configuration: four (4) on vertical centerline
      1. Lower, lower-middle: Rushton turbines, 32.5" (826 mm) diameter
      2. Upper-middle, upper: High-solidity hydrofoils, 34" (864 mm) diameter
3. Instrumentation was installed and available to make the following measurements:
   i. Temperature: Thermocouples were installed in thermowells to measure the temperature of the vessel contents (two probes) and baffle coolant supply and discharge temperature. Temperature data points were collected and stored using a Kaye Validator data logger.
   ii. Baffle coolant flow velocity was measured using an ultrasonic flowmeter with its transducer positioned on the coolant supply piping.
   iii. Agitator operating speed was set using the fermenter automation control system
      1. The automation system agitator speed control was calibrated during set-up using a hand-held optical tachometer.

Figure 8:
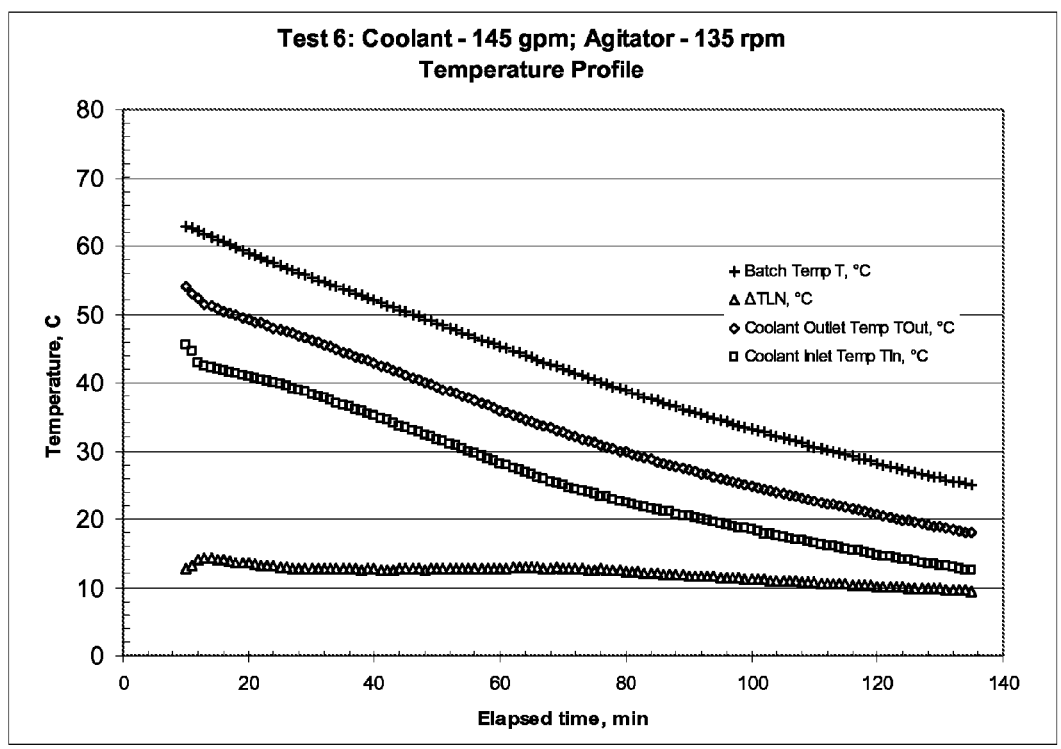
FIG. 8. Results from heat transfer experiment #1.

2. Agitator speed was verified during the tests using the same calibrated optical tachometer.
   iv. Agitator wire power draw was measured using a digital power meter to monitor all three legs of the power to the motor's AC variable frequency drive.
   v. The mass of the vessel contents was determined using calibrated differential pressure transducers.
4. The vessel was charged with 10,000 liters (kilograms) of de-ionized water at ambient conditions and the temperature of the contents was raised to 70° C. by direct steam injection. The final mass of the contents was recorded after steam injection to account for the addition of the resulting steam condensate.
5. The agitator speed was set at a value to deliver approximately 80% of full motor power for the first test; subsequent tests were conducted at speeds selected to yield power levels at approximately 50% and 25% of the initial value.
6. Coolant (chilled water) was re-circulated through the baffle assembly using a skid-mounted chiller and pump.
   i. Coolant flow was adjusted to the desired rate using a valve to throttle the discharge flow of the circulating pump.
   ii. Coolant velocity was measured using an ultrasonic flowmeter as noted above; volumetric flow rate was calculated as the product of velocity and pipe cross-sectional area.
   iii. Tests were conducted over a range of coolant flow rate.
   iv. The reported total coolant flow is equally divided among the six baffles by hydraulic balancing which is inherent in the design of the baffle coolant supply and discharge piping and headers.
7. Vessel batch temperature as well as coolant supply and discharge temperature were logged simultaneously at a rate of once per minute as the batch was cooled from 70° C. to 25° C. for a given set of coolant flow and agitator operating speed (FIG. 8).
8. The heat transfer rate Q over the course of the test is calculated from the data based on the mass of the batch and the minute-by-minute change in batch temperature using the relationship $$Q = m \cdot c_p \cdot \Delta T \cdot 60$$

where Q=heat transfer rate, BTU/hr
m=mass of vessel contents, $lb_m$
$c_p$=heat capacity of vessel contents, BTU/$lb_m$-° F.
$\Delta T$=temperature change per minute (e.g. $T_{t+1} - T_t$), ° F.

The overall heat transfer coefficient U is then calculated over the course of the test per the relationship $$Q = U \cdot A \cdot \Delta T_{ln}$$

where Q=heat transfer rate, BTU/hr
U=overall heat transfer coefficient, BTU/hr-$ft^2$-° F.
A=available area for heat transfer, $ft^2$
$\Delta T_{ln}$=log mean temperature driving force, ° F.

The above approach was used because the coolant inlet temperature did not stay constant but rather changed (decreased) over the course of the test and cycled with the operation of the chiller; coolant temperature was in the range of 54° C. to 12° C. for all tests. The resulting value of U likewise decreases over the course of the test and all comparisons are made at the batch temperature of interest, in this case, 37° C.

Note that the above approach which is based on the change in batch temperature is conservative since a heat balance based on the change (increase) in coolant temperature yielded a higher heat load.

Figure 9:
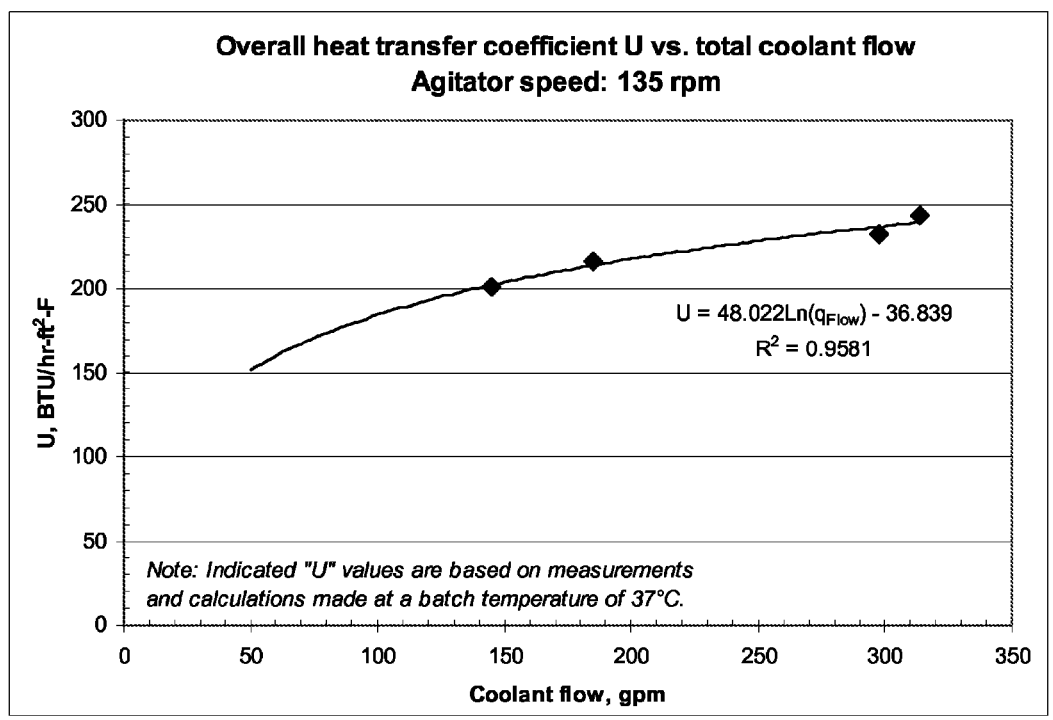
FIG. 9. Results from heat transfer experiment #2.

As shown in FIG. 9, the heat transfer system is capable of efficiently transferring heat from a reaction mixture. In the operating range of interest (37° C.), the tests yielded a U value in excess of 200 BTU/hr-$ft^2$-° F.; this compares very favorably to cooling-service values that are claimed for both external jackets (100-130) and internal structures (conventional helical coils and vertical tube bundles: 100; platecoils: 90-160). Even at low flow rates on the order of 100 gpm for six baffles (~17 gpm each) the measured heat transfer coefficient is greater than or equal to that for other devices.

Data collected at the maximum coolant flow rate tested and agitator power input levels associated with the operation of microbial fermenters (8-29 hp/kgal or 1.6-5.7 kW/$m^3$) indicated that overall heat transfer coefficient U was relatively constant (237±6 BTU/hr-$ft^2$-° F.) over the range examined.

All documents cited or referred to herein are hereby incorporated by reference in their entirety into this description. While the description provided herein may be presented in terms of the preferred embodiments, it is understood that variations and modifications will occur to those skilled in the art. Therefore, it is intended that the appended claims cover all such equivalent variations that come within the scope of the claimed subject matter.

What is claimed is:

1. A method for controlling the temperature of a process being carried out in a reaction vessel, the method comprising:
   1) providing a reaction vessel comprising at least one heat transfer baffle comprising:
      a. a first sub-assembly consisting essentially of a first material adjoined to a second material to form a first distribution channel,
      b. a second sub-assembly consisting essentially of a first material adjoined to a second material to form a second distribution channel,
      c. a closure bar that adjoins the first assembly and the second sub-assembly to one another; and
      d. a relief channel between the first sub-assembly and the second sub-assembly;
      wherein the closure bar sets the width of the relief channel, and the distribution channels and the relief channel do not communicate unless a leak forms within a distribution channel; and,
   2) circulating heat transfer medium through the at least one heat transfer baffle.

2. The method of claim 1 wherein the heat transfer medium is selected from the group consisting of steam, a pumpable fluid, water, glycol, a heat transfer oil, a refrigerant, and combinations thereof.

3. The method of claim 2 wherein the heat transfer medium is water.

4. The method of claim 1 wherein the process is selected from the group consisting of a chemical process, a pharmaceutical process, and a biological process.

5. The method of claim 4 wherein the biological process is selected from the group consisting of microbiological culture, mammalian cell culture, and plant cell culture.

6. The method of claim 4 wherein the process is at least one step in the production of a vaccine.

7. The method of claim 1 wherein the heat transfer baffle comprises two or more distinct compartments through which heat transfer media may be circulated independently of any other compartment.

8. The method of claim 1 wherein the at least one heat transfer baffle is adjoined to the reactor vessel.

9. The method of claim 8 wherein the one or more heat transfer baffles are adjoined to the reactor vessel through a substantially seamless joint boundary between the baffle and the vessel.

10. The method of claim 1 wherein at least one distribution channel is adjoined to a heat transfer media inlet header.

11. The method of claim 1 wherein at least one distribution channel is adjoined to a heat transfer media outlet header.

12. The method of claim 1 wherein at least one distribution channel is adjoined to a heat transfer media inlet header and a heat transfer media outlet header.

13. The method of claim 1 wherein the at least one heat transfer baffle is adjoined to the interior surface of a reaction vessel, at least one heat transfer media inlet header, and at least one heat transfer media outlet header; and the relief channel of each baffle is vented to the vessel exterior.

14. The method of claim 1 wherein the at least one heat transfer baffle is fixably attached to the interior surface of the reaction vessel such that when the vessel contains contents in motion resulting in stress upon the at least one heat transfer baffles, the stress is attenuated.

15. The method of claim 1 wherein the at least one heat transfer baffle is fixably attached to the interior surface of the reaction vessel at an angle relative to the interior wall or radius of the vessel, the angle being selected from the group consisting of about 5°, 10°, 15°, 20°, 25°, 30°, 35°, 40°, 45°, 50°, 55°, 60°, 65°, 70°, 75°, 80°, 85°, and 90°.

16. The method of claim 15 wherein the angle is about 60° relative to the interior wall or about 30° relative to the radius.

17. The method of claim 4 wherein the heat transfer baffle comprises two or more distinct compartments through which heat transfer media may be circulated independently of any other compartment.

18. The method of claim 4 wherein the at least one heat transfer baffle is adjoined to the reactor vessel.

19. The method of claim 4 wherein at least one distribution channel is adjoined to a heat transfer media inlet header and a heat transfer media outlet header.

20. The method of claim 4 wherein the at least one heat transfer baffle is adjoined to the interior surface of a reaction vessel, at least one heat transfer media inlet header, and at least one heat transfer media outlet header; and the relief channel of each baffle is vented to the vessel exterior.

* * * * *